United States Patent [19]
Steffan et al.

[11] Patent Number: 6,011,053
[45] Date of Patent: Jan. 4, 2000

[54] SUBSTITUTED INDOLE-1-CARBOTHIOIC ACID AMIDES AS NOVEL ANTIATHEROSCLEROTIC AGENTS

[75] Inventors: Robert J. Steffan, Langhorne, Pa.; Amedeo A. Failli, Princeton Junction, N.J.

[73] Assignee: American Home Products Corporation, Madison, N.J.

[21] Appl. No.: 09/145,942

[22] Filed: Sep. 2, 1998

Related U.S. Application Data

[60] Provisional application No. 60/056,287, Sep. 3, 1997.
[51] Int. Cl.[7] ............... C07D 209/08; C07D 403/12; A61K 31/40; A61K 31/415
[52] U.S. Cl. .............. 514/407; 514/419; 548/364.7; 548/500
[58] Field of Search .................. 548/364.7, 495, 548/500, 510; 514/407, 419, 415

[56] References Cited

U.S. PATENT DOCUMENTS 5,663,363  9/1997  Elokdah et al. ............... 548/320.5

FOREIGN PATENT DOCUMENTS 528146  2/1993  European Pat. Off. .

OTHER PUBLICATIONS

Barr et al., *Am. J. Med.*, 11:480–493 (1951).
Gofman et al., *Circulation*, 34:679–697 (1966).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest.*, 60:455–461 (1989).
Miller et al., *Br. Med. J.*, 282:1741–1744 (1981).
Picardo et al., *Arteriosclerosis.*, 6:434–441 (1986).
Glomset, *J. Lipid Res.*, 9:155–167 (1968).
Glass et al., *J. Biol. Chem.*, 258:7161–7167 (1983).
MacKinnon et al., *J. Biol. Chem.*, 261:2548–2552 (1986).
Grow and Fried, *J. Biol. Chem.*, 253:8034–8041 (1978).
Lagocki and Scanu, *J. Biol. Chem.*, 255:3701–3706 (1980).
Schaefer et al., *J. Lipid Res..*, 23:1259–1273 (1982).
Cockerill et al., *Arterioscler., Thromb., Vasc. Biol.* 15: (1995).
Muthusamy, S. et al., *J. Het. Chem.*, 28:759–763 (1991).
Papadopoulos, E. P. et al., *J. Org. Chem.*, 33:4551–4554 (1968).
Kikugawa, K. et al., *Chem. Pharm. Bull.* 21(5):1151–1155 (1973).

*Primary Examiner*—Mukund J. Shah
*Assistant Examiner*—Deepak R. Rao
*Attorney, Agent, or Firm*—Michael R. Nagy

[57] ABSTRACT

Antiatherosclerotic agents are provided having the structure:

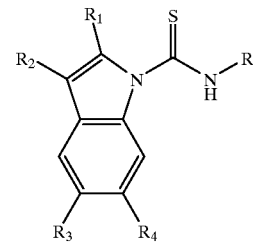

wherein
R is a lower alkyl of 1–6 carbon atoms,

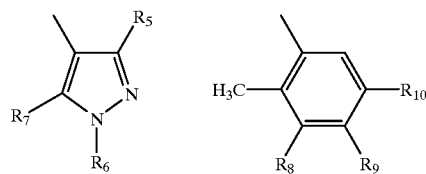

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

11 Claims, No Drawings

SUBSTITUTED INDOLE-1-CARBOTHIOIC ACID AMIDES AS NOVEL ANTIATHEROSCLEROTIC AGENTS

This application claims the benefit of U.S. Provisional Application No. 60/056,287 filed Sep. 3, 1997.

FIELD OF THE INVENTION

This invention is directed to antiatherosclerotic agents and more specifically to compounds, pharmaceutical compositions and methods for their use to elevate HDL cholesterol concentrations, which may be useful in the treatment of atherosclerotic conditions such as dyslipoproteinemias and coronary heart disease. More specifically, this invention relates to substituted indole-1-carbothioic acid amides useful as such compounds.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11 (1951) 480–483; Gofman et al. *Circulation.* 34 (1966), 679–697; Miller and Miller, *Lancet*, 1 (1975), 16–19; Gordon et al., *Circulation*, 79 (1989), 8–15; Stampfer et al., *N. Engl. J. Med.*, 325 (1991), 373–381; Badimon et al., *Lab. Invest.*, 60 (1989), 455–461). Atherosclerosis is the process of accumulation of cholesterol within the arterial wall which results in the occlusion, or stenosis, of coronary and cerebral arterial vessels and subsequent myocardial infarction and stroke. Angiographic studies have shown that elevated levels of some HDL particles in humans appear to be correlated to a decreased number of sites of stenosis in the coronary arteries of humans (Miller et al., *Br. Med. J.*, 282 (1981), 1741–1744).

There are several mechanisms by which elevated HDL levels may protect against the progression of atherosclerosis. Studies in vitro have shown that HDL is capable of removing cholesterol from cells (Picardo et al., *Arteriosclerosis*, 6 (1986), 434–441). Data of this nature suggest that one antiatherogenic property of HDL may lie in its ability to deplete tissue of excess free cholesterol and eventually lead to the delivery of this cholesterol to the liver (Glomset, *J. Lipid Res.*, 9 (1968), 155–167). This has been supported by experiments showing the efficient transfer of cholesterol from HDL to the liver (Glass et al., *J. Biol. Chem.*, 258 (1983), 7161–7167; McKinnon et al., *J. Biol. Chem.*, 261 (1986), 2548–2552). In addition, HDL may serve as a reservoir in the circulation for apoproteins necessary for the rapid metabolism of triglyceride-rich lipoproteins (Grow and Fried, *J. Biol. Chem.*, 253, (1978), 1834–1841; Lagocki and Scanu, *J. Biol. Chem.*, 255 (1980), 3701–3706; and Schaefer et al., *J. Lipid Res.*, 23 (1982), 1259–1273). More recently, as a possible mechanism for protection against the development of atherosclerosis, Cockerill et. al. *Arterioscler., Thromb., Vasc. Biol*, 15, (1995), 1987–1994 have demonstrated that plasma HDL's inhibit cytokine-induced expression of endothelial cell adhesion molecules (VCAM-1 and ICAM-1) in a concentration dependent and cell specific manner. Accordingly, it follows that compounds which increase HDL cholesterol concentrations would be useful as anti-atherosclerotic agents, useful particularly in the treatment of dyslipoproteinimias and coronary heart disease.

Certain indole-1-carbothioic acid amides and their derivatives have been disclosed in the prior art. For example, the use of indole-1-carbothioic acid amides as intermediates in the synthesis of benzothiazoles has been discussed in *J. Het. Chem.*, 28 (1991) 759–763. *J. Org. Chem.*, 33 (1968), 4551–4554, describes the synthesis of indole-1-carbothioic acid amides. However, no utility for the compound is stated. Lastly, the use of a series of indole-1-carbothioic acid amides as inhibitors of platelet aggregation is disclosed in *Chem. Pharm. Bull.*, 21 (1973), 1151–1155. However, the prior art contains no disclosure or suggestion of the use of the present substituted indole-1-carbothioic acid amides, nor their use as antiatherosclerotic agents.

SUMMARY OF THE INVENTION

The present invention relates to antiatherosclerotic agents comprising substituted indole-1-carbothioic acid amides represented by formula 1:

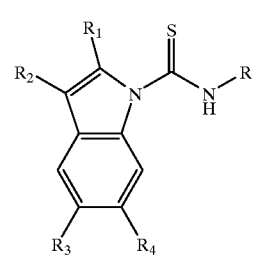

1 wherein

R is a lower alkyl of 1–6 carbon atoms,

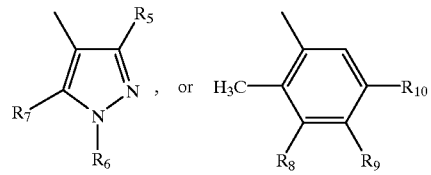

wherein $R_5$, $R_6$ and $R_7$ are lower alkyl of 1–6 carbon atoms; and $R_8$, $R_9$, $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

The present invention is further directed to methods for elevating the HDL concentration and treating atherosclerosis and associated conditions, such as coronary heart disease and dysliproteinemias in a mammal in need thereof. The present methods comprise administering to the mammal an effective amount of the antiatherosclerotic agents represented by formula 1:

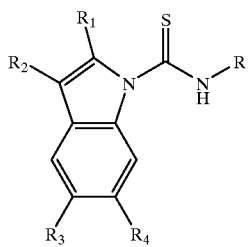

wherein

R is a lower alkyl of 1–6 carbon atoms,

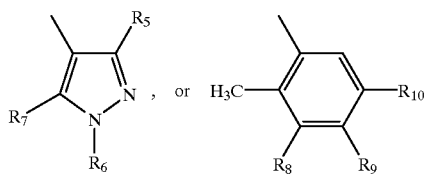

wherein $R_5$, $R_6$ and $R_7$ are lower alkyl of 1–6 carbon atoms; and $R_8$, $R_9$, $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

DETAILED DESCRIPTION OF THE INVENTION

Preferably, the antiatherosclerotic agents of the present invention are: 6-chloro-indole-1-carbothioic acid isopropylamide; 5-chloro-indole-1-carbothioic acid (1,3,5-trimethyl-1H-pyrazol-4-yl)-amide; N-(5-chloro-2-methyl-phenyl)-2-methyl-indole-1-carbothioic acid amide; and N-(5-chloro-2-methyl-phenyl)-2-,3-dimethyl-1H-indole-1-carbothioic acid amide.

The pharmaceutically acceptable salts of the present compounds are those derived from such inorganic cations such as sodium, potassium, and the like; organic bases such as mono-, di-, and trialkyl amino of 1–6 carbon atoms per alkyl group, and mono-, di - and trihydroxy alkyl amines of 1–6 carbon atoms per alkyl group, and the like; and organic and inorganic acids, such as: acetic, lactic, citric, tartaric, succinic, maleic, fumaric, malic, malonic, gluconic, hydrochloric, hydrobromic, phosphoric, nitric, sulfuric, methane sulfuric, toluene sulfonic and similarly known acceptable acids.

The term "lower alkyl" as used herein includes both straight chain, as well as branched moieties. The term "halogen" includes fluorine, chlorine, bromine, and iodine.

The compounds of the present invention may be prepared by reacting the potassium salt of an appropriately substituted indole with a substituted isothiocyanate using conditions such as those described by S. Muthuswamy et. al., *J. Het. Chem.*, 28, (1991), 759 as shown in Scheme 1. The substituted isothiocyanates of heteroaryl and aryl systems are either commercially available, are known in the art or may be prepared by procedures analogous to those in the literature for known compounds such as those described in Linders, J. T. M, *J. Lab. Comp*, 31, (1992), 671. The substituted indoles are either commercially available or are known in the art or may be prepared by procedures analogous to those in the literature for known compounds.

Scheme 1

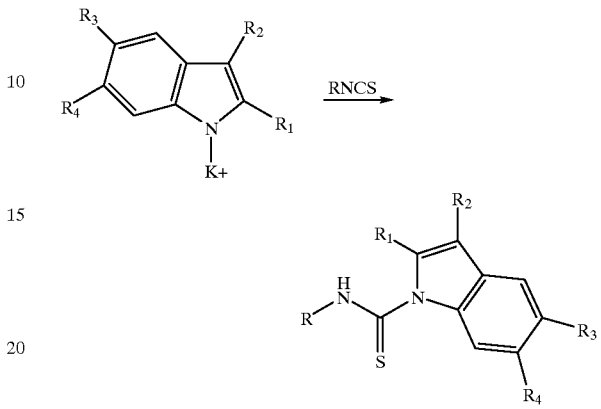

wherein R, $R_1$, $R_2$, $R_3$, and $R_4$ are as described above for formula 1.

Representative compounds of this invention were evaluated in an in vivo standard pharmacological test procedure which measured the ability of the present compounds to elevate HDL cholesterol levels. The following describes the procedure used and results obtained. Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. Typical doses of the test substances were 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzene sulfonate in a pH 6.5 buffer. In the reaction cholesterol was oxidized to produce hydrogen peroxide which was used to form a quinoneimine dye. The concentration of dye formed was measured spectrophotometrically by absorbance at 490 nm after incubation at 25° C. for 30 minutes. The concentration of cholesterol was determined for each serum sample relative to a commercial standard from Sigma.

HDL cholesterol concentrations in serum were determined by separation of lipoprotein classes by fast protein liquid chromatography (FPLC) by a modification of the method of Kieft et al., *J. Lipid Res.*, 32, (1991), 859–866. Using this methodology, 25 mL of serum was injected onto Superose 12 and Superose 6 (available from Pharmacia), in series, with a column buffer of 0.05 M Tris (2-amino-2-hydroxymethyl-1,3-propanediol) and 0.15 M sodium chloride at a flow rate of 0.5 mL/min. The eluted sample was mixed on line with Boehringer-Mannheim cholesterol reagent pumped at 0.2 mL/min. The combined eluents were mixed and incubated on line through a knitted coil (available from Applied Biosciences) maintained at a temperature of 45° C. The eluent was monitored by measuring absorbance at 490 nm and gives a continous absorbance signal proportional to the cholesterol concentration. The relative concentration for each lipoprotein class was calculated as the percent of total absorbance. HDL cholesterol concentration in serum, was calculated as the percent of total cholesterol as determined by FPLC multiplied by the total serum cholesterol concentration.

Test compounds were administered at a dose of 100 mg/kg for 8 days. The increase in serum concentrations of HDL cholesterol are summarized in Table 1.

TABLE 1

| Example Number | HDL Cholesterol Level Increase (%) |
|---|---|
| 1 | 9 |
| 2 | 66 |
| 3 | 60 |
| 4 | 51 |
| 5 | 38 |

The results set forth in Table 1 demonstrate that the compounds of this invention are useful for raising the serum concentration of HDL cholesterol. Therefore, the present compounds would likewise be useful for treating or inhibiting atherosclerosis, and related cardiovascular disease, or dysliproteinemias. Moreover, it is believed that the present compounds are useful for improving the HDL/LDL cholesterol ratio and several metabolic conditions associated with low concentrations of HDL, such as low HDL levels in the absence of dyslipidemia, metabolic syndrome, non-insulin dependent diabetes mellitus (NIDDM), familial combined hyperlipidemia, familial hypertriglyceridemia and dyslipidemia in peripheral vascular disease (PVD).

The compounds of the present invention may be administered orally or parentally, neat or in combination with conventional pharmaceutical carriers. Applicable solid carriers can include one or more substances which may also act as flavoring agents, lubricants, solublizers, suspending agents, fillers, glidants, compression aids, binders, tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may preferably contain up to 99% of the active ingredient. Any of the solid carriers known to those skilled in the art may be used with the compounds of the invention. Particularly suitable solid carriers include, e.g., calcium phosphate, magnesium stearate, talc, sugars, lactose, dextrin, starch, gelatin, cellulose, methyl cellulose, sodium carboxy methyl cellulose, polyvinlpyrrolidone, low melting waxes and ion exchange resins.

Liquid carriers may be used to prepare solutions, suspensions, emulsions, syrups and elixirs containing the compounds of the present invention. The compounds of this invention may be dissolved or suspended in a pharmaceutically acceptable liquid carrier such as water, an organic solvent, a mixture of both or pharmaceutically acceptable oils or fats. The liquid carrier may contain other suitable pharmaceutical additives, such as solublizers, emulsifiers, buffers, preservatives, sweeteners, flavoring agents, suspending agents, thickening agents, colors, viscosity regulators, stabilizers or osmo-regulators. Examples of suitable liquid carriers for oral and parenteral administration include water, alcohols (including monohydric alcohols and polyhydric alcohols, e.g., glycols) and their derivatives and oils (e.g., fractionated coconut oil and arachis oil). For parenteral administration, the carrier may also be an oily ester such as ethyl oleate and isopropyl myristate.

Sterile liquid carriers are used in sterile liquid form for parenteral administration. Liquid pharmaceutical compositions which are sterile solutions or suspensions can be utilized by, e.g., intramuscular, intraperitoneal or subcutaneous injection. Sterile solutions can also be administered intravenously.

Preferably, the pharmaceutical compositions containing the compounds of the present invention are in unit dosage form, e.g. as tablets or capsules. In such form, the compositions may be sub-divided inr unit doses containing appropriate quantities of the present compounds. The unit dosage forms can be packaged compositions, e.g., packeted powders, vials, ampoules, prefilled syringes or sachets containing liquids. Alternatively, the unit dosage form can be, e.g., a capsule or tablet itself, or it can be the appropriate number of any such compositions in package form.

The therapeutically effective amount of the present compounds that is administered and the dosage regimen depends on a variety of factors, including the weight, age, sex, medical condition of the subject, the severity of the disease, the route and frequency of the administration and the specific compound employed. Therefore, the specific therapeutically effective amount to be administered may vary widely. However, it is believed that pharmaceutical compositions may contain the compounds of the present invention in a range of about about 0.1 to about 2000 mg, preferably in the range of about 0.5 to about 500 mg and more preferably in the range of about 1.0 to about 100 mg/kg body weight.

The following non-limiting examples illustrate the preparation of representative compounds of the present invention.

EXAMPLE 1

5-Chloro-indole-1-carbothioic acid isopropylamide

A stirred slurry of hexane washed potassium hydride (0.87 g, 21.8 mmol) in 50 mL of dry THF was treated portionwise with 5-chloroindole (3.3 g, 21.8 mmol). The mixture was heated at reflux until a clear solution was obtained. A solution of isopropyl isothiocyanate (2.2 g, 21.8 mmol) in 5 mL THF was slowly added and stirring was continued for 1 hour. The solvent was evaporated and the residue partitioned between EtOAc and 1N HCl. The organic layer was washed with brine, dried over $Na_2SO_4$ and concentrated in vacuo. The amber solids were recrystallized from EtOH to provide 3.4 g of the title compound as a tan solid, m.p. 135° C. (62% of theory).

NMR (DMSO-$d_6$, 400 MHz): 1.30 (d, 6H, CHCH$_3$), 4.59 (m, 1H, CH), 6.65 (d, 1H ArH), 7.73 (dd, 1H, ArH), 7.67 (d, 1H, ArH), 7.82 (d, 1H, ArH), 8.03 (d, 1H, ArH), 9.97 (s, 1H, NH).

MS [EI, m/z]: 252 [M]$^+$, 151 [b.p.].

Anal. Calc'd. for $C_{12}H_{13}ClN_2S$: C, 57.02; H, 5.18; N, 11.08 Found: C, 57.29; H, 5.06; N, 11.15.

EXAMPLE 2

6-Chloro-indole-1-carbothioic acid isopropylamide

A stirred slurry of hexane washed potassium hydride (0.56 g, 13.9 mmol) in 25 mL of dry THF was treated portionwise with 6-chloroindole (2.0 g, 13.9 mmol). The mixture was heated at reflux until a clear solution was obtained. A solution of isopropyl isothiocyanate (1.4 g, 13.9 mmol) in 5 mL THF was slowly added and stirring was continued for 1 hour. The solvent was evaporated and the residue partitioned between EtOAc and 1N HCl. The organic layer was washed with brine, dried over $Na_2SO_4$ and concentrated in vacuo. The residual amber solids were recrystallized from EtOH to provide 2.2 g of the title compound as a cream colored solid, m.p. 92–93° C. (63% of theory).

NMR (DMSO-$d_6$, 400 MHz): 1.30 (d, 6H, CHCH$_3$), 4.535 (m, 1H, CH), 6.685 (d, 1H ArH), 7.22 (m, 1H, ArH), 7.62 (d, 1H, ArH), 7.785 (d, 1H, ArH), 8.11 (s, 1H, ArH), 9.98 (s, 1H, NH).

MS [EI, m/z]: 252 [M]$^+$, 151 [b.p.].

Anal. Calc'd. for $C_{12}H_{13}ClN_2S$: C, 57.02; H, 5.18; N, 11.08 Found: C, 57.24; H, 5.05; N, 10.89.

EXAMPLE 3

5-Chloro-indole-1-carbothioic acid (1,3,5-trimethyl-1H-pyrazol-4-yl)amide

Step A: (1,3,5-trimethyl-pyrazol-4-yl)-isothiocyanate

A mixture of 4-amino-1,3,5-trimethylpyrazole (1.32 g, 10.6 mmol) in 50 mL each of CHCl$_3$ and saturated aqueous NaHCO$_3$ was treated dropwise with thiophosgene (0.812 mL, 10.6 mmol) and stirred vigorously for 20 minutes. The layers were separated and the organic phase was washed with brine. After drying (Na$_2$SO$_4$), the solvent was evaporated in vacuo to provide the title compound (1.8 g, brown oil) suitable for use directly in the next step.

NMR (DMSO-$d_6$, 300 MHz): 2.12 (s, 3H, ArCH$_3$), 2.22 (s, 3H, ArCH$_3$), 3.63 (s, 3H, NHCH$_3$).

Step B: 5-Chloro-indole-1-carbothioic acid (1,3,5-trimethyl-1H-pyrazol-4-yl)-amide A stirred slurry of hexane washed potassium hydride (0.423 g, 10.6 mmol) in 50 mL of dry THF was treated portionwise with 5-chloroindole (1.6 g, 10.6 mmol). The mixture was stirred until a clear solution was obtained. A solution of (1,3,5-trimethyl-pyrazol-4-yl)-isothiocyanate (1.8 g, 10.6 mmol) of step A in 5 mL THF was slowly added and stirring was continued for 1 hour. The reaction mixture was concentrated in vacuo and the residue partitioned between EtOAc and 1N HCl. The organic layer was washed with brine, dried over Na$_2$SO$_4$ and concentrated in vacuo. The residual solid foam was triturated with Et$_2$O-hexane overnight to provide 2.0 g of the title compound as a tan solid, m.p. 165–166° C. (59% of theory).

NMR (DMSO-$d_6$, 400 MHz): 2.04 (s, 3H, ArCH$_3$), 2.12 (s, 3H, ArCH$_3$), 3.68 (s, 3H, ArCH$_3$), 6.735 (d, 1H ArH), 7.305 (dd, 1H, ArH), 7.716 (d, 1H, ArH), 7.995 (d, 1H, ArH), 8.26 (d, 1H, ArH), 10.87 (s, 1H, NH).

MS [EI, m/z]: 318 [M$^+$, b.p].

Anal. Calc'd. for $C_{15}H_{15}ClN_4S$: C, 56.51; H, 4.74; N, 17.57 Found: C, 56.77; H, 4.75; N, 17.10.

EXAMPLE 4

N-(5-Chloro-2-methyl-phenyl)-2-methyl-1H-indole-1-carbothioic acid amide

A stirred slurry of hexane washed potassium hydride (1.51 g, 38 mmol) in 10 mL of dry THF was treated dropwise with a solution of 2-methylindole (5.0 g, 38 mmol) in 30 mL THF. The mixture was stirred until hydrogen evolution ceased. To the dark red solution was slowly added 5-chloro-2-methylphenylisothiocyanate (7 g, 38 mmol) and stirring was continued for 16 hours. The reaction mixture was concentrated in vacuo and the residue partitioned between EtOAc and 1N HCl. The organic layer was washed with brine, dried over Na$_2$SO$_4$ and concentrated in vacuo to give 11.5 g of rose colored solids. The solids were dissolved in Et$_2$O and clarified with Norite-A. Hexane was added to the filtered solution and the precipitate was collected and dried to give 7.0 of the title compound as a light yellow solid, m.p. 121–122° C. (53% of theory).

NMR (DMSO-$d_6$, 400 MHz): 2.306 (s, 3H, ArCH$_3$), 2.593 (s, 3H, ArCH$_3$), 6.35 (s, 1H, ArH), 7.12 (m, 1H, ArH), 7.18 (m, 1H, ArH), 7.39 (m, 2H, ArH), 7.5 (m, 2H, ArH), 7.75 (d, 1H, ArH), 11.83 (s, 1H, NH).

MS [EI, m/z]: 314 [M]$^+$, 183, 148, 131 [b.p.].

Anal. Calc'd. for $C_{17}H_{15}ClN_2S$: C, 65.55; H, 5.23; N, 8.57 Found: C, 65.14; H, 5.19; N, 8.31.

EXAMPLE 5

N-(5-Chloro-2-methylphenyl)-2,3-dimethyl-1H-indole-1-carbothioic acid amide

A stirred slurry of hexane washed potassium hydride (1.38 g, 34.5 mmol) in 10 mL of dry THF was treated dropwise with a solution of 2,3-dimethylindole (5.0 g, 34.5 mmol) in 30 mL THF. The mixture was stirred until a clear solution was obtained. A solution of 5-chloro-2-methylphenylisothiocyanate (6.3 g, 34.5 mmol) in 5 mL THF was slowly added and stirring was continued for 16 hours. The reaction mixture was concentrated in vacuo and the residue partitioned between EtOAc and 1N HCl. The organic layer was washed with brine, dried over Na$_2$SO$_4$ and concentrated in vacuo. The residual solid was triturated with Et$_2$O-hexane overnight to provide 7.5 g of the title compound as a light yellow solid, m.p. 115° C. (67% of theory).

NMR (DMSO-$d_6$, 400 MHz): 2.226 (s, 3H, ArCH$_3$), 2.229 (s, 3H, ArCH$_3$), 2.533 (s, 3H, ArCH$_3$), 7.16 (m, 2H ArH), 7.38 (m, 2H, ArH), 7.5 (m, 2H, ArH), 7.768 (d, 1H, ArH), 11.65 (s, 1H, NH).

MS [EI, m/z]: 328 [M]$^+$, 183, 145 [b.p.].

Anal. Calc'd. for $C_{18}H_{17}ClN_2S$: C, 65.74; H, 5.21; N, 8.52 Found: C, 65.41; H, 5.14; N, 8.51.

The present invention may be embodied in other specific forms without departing from the spirit and essential attributes thereof and accordingly, reference should be made to the appended claims, rather than to the foregoing specification, as indicating the scope of the invention.

What is claimed is:

1. Antiatherosclerotic agents having the following structure:

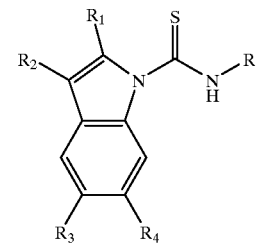

wherein

R is a lower alkyl of 1–6 carbon atoms,

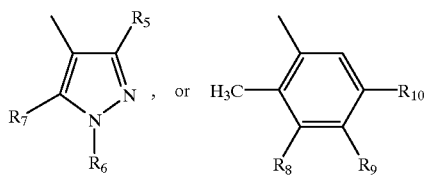

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

2. The antiatherosclerotic agent of claim 1, which is 6-chloro-indole-1-carbothioic acid isopropyl-amide.

3. The antiatherosclerotic agent of claim 1, which is 5-chloro-indole-1-carbothioic acid (1,3,5-trimethyl-1H-pyrazol-4-yl)-amide.

4. The antiatherosclerotic agent of claim 1, which is 5-chloro-indole-1-carbothioic acid isopropyl-amide.

5. The antiatherosclerotic agent of claim 1, which is N-(5-chloro-2-methylphenyl)-2-methyl-1H-indole-1-carbothioic acid amide.

6. The antiatherosclerotic agent of claim 1, which is N-(5-chloro-2-methylphenyl)-2,3-dimethyl-1H-indole-1-carbothioic acid amide.

7. A method of elevating the concentration of HDL cholesterol in a mammal in need thereof, comprising administering to said mammal an effective amount of a compound of the structure:

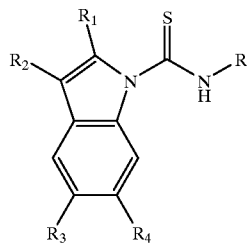

wherein
R is a lower alkyl of 1–6 carbon atoms,

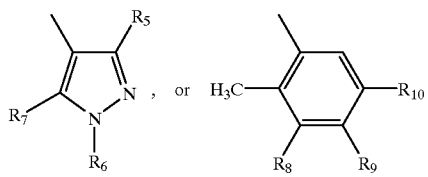

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

8. A method of treating atherosclerosis in a mammal in need thereof, which comprises administering to said mammal an anti-atherosclerotic effective amount of a compound of the structure:

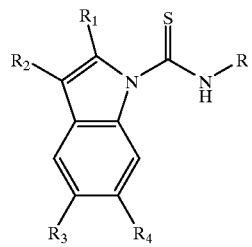

wherein
R is a lower alkyl of 1–6 carbon atoms,

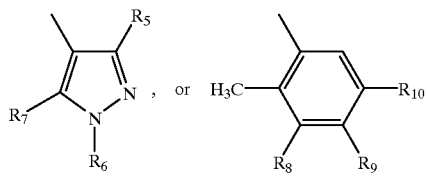

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

9. A method of treating dyslipoproteinemia in a mammal in need thereof, which comprises administering to said mammal an anti-dyslipoproteinemic effective amount of a compound of the structure:

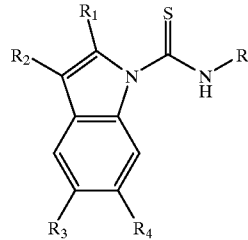

wherein
R is a lower alkyl of 1–6 carbon atoms,

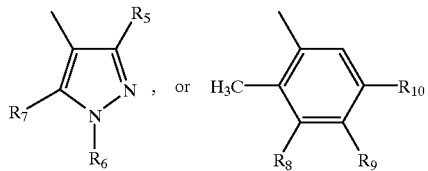

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

10. A method of treating cardiovascular disease in a mammal in need thereof, which comprises administering to said mammal anti-cardiovascular disease effective amount of a compound of the structure:

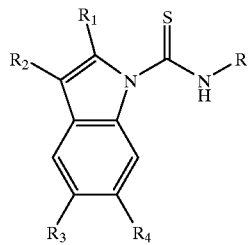

wherein

R is a lower alkyl of 1–6 carbon atoms,

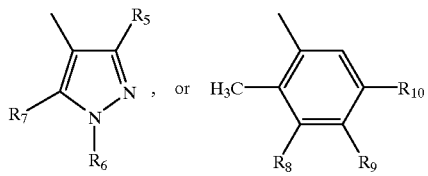

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

11. A pharmaceutical composition which comprises an antiatherosclerotic agent of the structure:

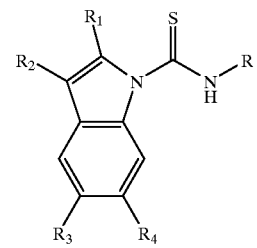

wherein

R is a lower alkyl of 1–6 carbon atoms,

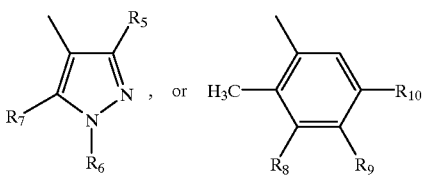

wherein $R_5$, $R_6$, and $R_7$ are lower alkyl of 1–6 carbon atoms; and $R_8$, $R_9$ and $R_{10}$ are each, independently, hydrogen or halogen;

$R_1$ and $R_2$ are each, independently, hydrogen or a lower alkyl of 1–6 carbon atoms; and $R_3$ and $R_4$ are each, independently, hydrogen, a lower alkyl of 1–6 carbon atoms or halogen;

or a pharmaceutically acceptable salt thereof.

* * * * *